(12) United States Patent
Kuronen et al.

(10) Patent No.: US 11,673,021 B2
(45) Date of Patent: Jun. 13, 2023

(54) DEVICE FOR THE CARE OF RESPIRATORY WELLBEING AND FOR TRAINING AND THE IMPROVEMENT OF RESPIRATORY FUNCTION

(71) Applicant: WellO2 Oy, Tampere (FI)

(72) Inventors: Ilpo Kuronen, Kuopio (FI); Siamäk Naghian, Lapinlahti (FI)

(73) Assignee: WellO2 Oy, Tampere (FI)

( * ) Notice: Subject to any disclaimer, the term of this patent is extended or adjusted under 35 U.S.C. 154(b) by 592 days.

(21) Appl. No.: 16/685,736

(22) Filed: Nov. 15, 2019

(65) Prior Publication Data
US 2020/0155898 A1 May 21, 2020

(30) Foreign Application Priority Data

Nov. 19, 2018 (FI) ........................................ 20185974

(51) Int. Cl.
*A63B 23/18* (2006.01)
*A61M 16/10* (2006.01)
(Continued)

(52) U.S. Cl.
CPC ............ *A63B 23/18* (2013.01); *A61B 5/0871* (2013.01); *A61B 5/091* (2013.01); *A61B 5/486* (2013.01);
(Continued)

(58) Field of Classification Search
CPC .............. A63B 23/18; A63B 2213/005; A63B 24/0087; A63B 21/00069; A63B 21/008;
(Continued)

(56) References Cited

U.S. PATENT DOCUMENTS 3,250,270 A * 5/1966 Bloom ..................... A61B 5/09
374/31
2010/0078024 A1* 4/2010 Andrieux ............ A61M 16/201
128/204.21

(Continued)

FOREIGN PATENT DOCUMENTS

| CH | 687296 A5 | 11/1996 |
| CN | 1166369 A | 12/1997 |

(Continued)

OTHER PUBLICATIONS

Finnish Patent and Registration Office, Search Report and Office Action in FI 20185974, dated Jun. 17, 2019, 9 pages.
(Continued)

*Primary Examiner* — Elliot S Ruddie
(74) *Attorney, Agent, or Firm* — Ziegler IP Law Group, LLC (57) ABSTRACT

A device including a first flow channel, a second flow channel and a body part including an inner volume. A first space of the inner volume is adapted to be filled with liquid and a second space of the inner volume is arranged to receive steam. The device further includes means for conveying a gas flow from the steam space of the inner volume via the first flow channel to the outside of the device during inhalation and means for conveying the exhaled gas flow from the outside of the device via the second flow channel to the first space of the inner volume. The device further includes means for measuring a flow and a temperature of an airflow, and means for adjusting the flow of the airflow mechanically and/or automatically. The present disclosure further relates to a method and a system.

14 Claims, 4 Drawing Sheets

(51) Int. Cl.
  *A61B 5/087* (2006.01)
  *A61B 5/091* (2006.01)
  *A61B 5/00* (2006.01)
  *A61M 16/20* (2006.01)
  *A61M 16/00* (2006.01)

(52) U.S. Cl.
  CPC ........ *A61M 16/109* (2014.02); *A61M 16/208* (2013.01); *A61B 2505/09* (2013.01); *A61M 2016/0036* (2013.01); *A61M 2205/50* (2013.01); *A63B 2213/005* (2013.01)

(58) Field of Classification Search
  CPC ........ A63B 21/0085; A63B 2024/0065; A63B 2024/0093; A63B 2220/72; A63B 2225/20; A63B 2225/50; A63B 2225/54; A63B 2230/04; A63B 2230/06; A63B 2230/40; A63B 2230/42; A63B 2230/433; A63B 2225/64; A63B 2230/50; A61B 5/087–095; A61B 5/486; A61B 2505/09; A61M 16/109; A61M 16/20–209; A61M 2016/0036; A61M 2205/50; A61M 11/04; A61M 11/042; A61M 2016/0027; A61M 16/16; A61M 11/044; A61M 16/0045; A61M 2016/003; A61M 2205/3331; A61M 2205/3334; A61M 2205/3348; A61M 2205/3368; A61M 2205/3633; A61M 2205/8206; A61M 15/00; A61M 15/002; A61M 15/02; A61M 16/00; A61M 16/0006; A61M 16/024
  USPC .......................................................... 482/13
  See application file for complete search history.

(56) References Cited

U.S. PATENT DOCUMENTS

| | | | |
|---|---|---|---|
| 2015/0283352 A1* | 10/2015 | Karkkainen | A63B 21/0088 |
| | | | 128/203.26 |
| 2018/0008790 A1 | 1/2018 | Costella et al. | |
| 2019/0150849 A1* | 5/2019 | Yorke | A61B 5/14551 |

FOREIGN PATENT DOCUMENTS

| | | | | |
|---|---|---|---|---|
| CN | 2297204 Y | 11/1998 | | |
| CN | 102355916 A | 2/2012 | | |
| CN | 103251410 A | 8/2013 | | |
| CN | 107362506 A | 11/2017 | | |
| CN | 107427651 A | 12/2017 | | |
| EP | 2708260 A1 | 3/2014 | | |
| FR | 779571 A | 4/1935 | | |
| JP | 2015528357 A | 9/2015 | | |
| WO | WO-2016001926 A1 * | 1/2016 | ............ | A24F 40/10 |
| WO | 2016115465 A1 | 7/2016 | | |
| WO | 2017072036 A1 | 5/2017 | | |

OTHER PUBLICATIONS

Extended European Search Report, Application No. 19207630.5, dated Apr. 15, 2020, 9 pages.
China National Intellectual Property, First Office Action, Application No. 2019111286698, dated Aug. 24, 2022, 8 pages, English Translation 9 pages.
Intellectual Property India, Examination Report, Application No. 201934044421, dated Sep. 30, 2022, 7 pages.
Patent Office of the People's Republic of China, Search Report, application No. 2019111286698, dated Aug. 24, 2022, 3 pages.
Japanese Patent Office, Notification of Reason for Refusal; JP Patent Application No. 2019-209051, dated Dec. 13, 2022, 10 pages.

* cited by examiner

DEVICE FOR THE CARE OF RESPIRATORY WELLBEING AND FOR TRAINING AND THE IMPROVEMENT OF RESPIRATORY FUNCTION

FIELD

The aspects of the disclosed embodiments relate to a device for wellness of respiratory and/or for training and improvement of pulmonary function, comprising at least a first flow channel and a liquid space for liquid. Furthermore, the aspects of the disclosed embodiments relate to a method and a system for monitoring and controlling air and steam flows and temperature in a device comprising at least a first flow channel and a liquid space for liquid.

BACKGROUND

Respiratory problems are still huge global and increasingly costly phenomena. Even though, severe asthma incidences have been in decline in developed countries due to better medication, the atypical asthma incidences have increased presumably due to poor in- and outdoor air quality. Air-born particles, nitric dioxides and ozone are known to have an impact on asthma exacerbations. Also, it has been suggested that they present a significant reason for development of asthma. Accumulation of phlegm into airways because of allergies or poor air quality exposes a person to airway infections. For asthmatics and COPD patients, phlegm exerts a barrier to inhalable drugs to get contact with the epithelium beneath the mucus layer. This may lead to ineffective medication and even attenuation of side effects.

In obstructive pulmonary diseases, such as asthma and chronic obstructive pulmonary disease (COPD), the obstruction of the airways restricts the airflow. In asthma, allergic reaction causes response in bronchial tubes leading to thickening of the epithelium and narrowing of the lumen, manifesting acute respiration problem. COPD instead is manifested by chronic inflammation in alveoli and bronchial tubes. The inflammation, both in asthma and COPD, causes permanent changes in morphology of bronchial tubes, and chest motility. Accumulation of mucus is common in those diseases, and in many cases, its clearance is hampered by dysfunction of ciliary motility. Mucus preserves harmful cell debris and irritating components and exposes to viral and bacterial airway infections and exacerbations. Therefore, it is utmost important to look after adequate mucus clearance, especially during exacerbations. In asthma, the bronchial tubes are obstructed as a result of inflammation. In COPD, the symptoms are caused by long-lasting inflammation. In COPD, the symptoms include shortness of breath and mucus in the airways. Furthermore, the symptoms can be aggravated by thoracic muscle tension resulting from the diseases. Moreover, in acute respiratory tract infections, the bronchial tubes of the patients may easily become irritated and inflamed. Pressure gradient in the small airways removes mucus towards larger airways from which the mucus is easier to be coughed out. Coughing removes mucus and makes it rise higher in the airways. In asthmatic patients, allergic reaction contacts the bronchial tubes and blocks airflow. Irritation, instead, enhances accumulation of mucus into the bronchial tubes. This exposes the patient to airway infections and pneumonia.

Bottle blowing is a decades old remedy for removing mucus from the airways. Also, steam inhaling has been used since 60's to alleviate upper airways' congestion. When blowing into a bottle, the patient blows through a hose into a bottle that contains water. Such resisted blowing removes mucus and opens bronchial tubes. Steam inhalation, in turn, moisturises the bronchial tubes and makes the mucus more fluid and easier to be coughed out.

Pulmonary diseases increase cardiac load and aggravate heart-related diseases, such as the occurrence of arrhythmias (for example, atrial fibrillation).

Care of the respiratory diseases is based on inhalable drugs which are administered into the airways with help of inhalers or nebulizers. Also, steam inhalers have been used to alleviate congestion of the airways. Boiled water, instead, is not recommended for steam inhaling due to potential risk of scalding.

BRIEF SUMMARY

It is an aim of the aspects of the disclosed embodiments to provide an improved steam inhaler. It is beneficial to monitor and control temperature and airflow of the inhaled steam to provide adequate energy on the airways without causing damage. Therefore, the device according to the present disclosure has sensors in connection with an airflow channel to measure airflow and temperature of inhaled airflow and steam. In accordance with an embodiment, the sensors are integrated into the airflow channel. The measured parameters are used to calculate an index which tells substantially exactly the exposure time for the user. The measured parameters can also be used to inform on correct use of the device. The recorded parameters can be stored, analysed and monitored for further analysis of the user's progression and her/his wellness training programs. The aspects of the disclosed embodiments resisted exhalation and inhalation, and steam inhalation which is a part of the inhalation process. Thus, these methods work in synergy and make it possible to deliver many positive effects on respiration.

Blowing against resistance is effective in opening particularly the small bronchial tubes in the lower part of the lungs and activating the outer costal muscles that compress positive inter thoracic pressure and airflow on exhaling. As a result, in the inhalation step, moist steam can better reach the small bronchial tubes, and at the same time it makes the mucus more fluid and more easily removable by coughing.

The aspects of the disclosed embodiments are based on the mechanical airflow resistance on exhalation and inhalation. Additionally, the mechanics of the present disclosure allows the steam to flow into the airways on inhalation. Thus, the effect of a drug or another active agent possibly carried by the moist steam can be delivered deeper into the airways. In accordance with an embodiment, counter pressure breathing, and steam inhalation are combined to improve respiratory functions. In addition, hyperthermia can be monitored and controlled.

The aspects of the disclosed embodiments can be used, not only in medical applications but also in sports and wellbeing applications, to improve respiratory functions.

In accordance with an embodiment, at least flow of an inhaled air and temperature of the inhaled airflow are measured to obtain first measurement parameters. In accordance with an embodiment, also airflow rate and temperature of an exhaled airflow are measured to obtain second measurement parameters. At least one index based on said first and/or second measurement parameters can be used for monitoring hyperthermia in airways. The at least one index is a value relating to a thermal exposure.

The at least one index can be selected based on the source date comprising:

calculated amount of energy gained during the inhaling,
calculated amount of energy used during the exhaling,
tidal volume (TV),
inspiratory reserve volume (IRV),
expiratory reserve volume (ERV),
residual volume (RV),
lung total capacity (LTC),
Heart rate variation
maximal inspiratory pressure (MIP),
maximal expiratory pressure (MEP),
maximal inspiratory flow (MIF), and/or
maximal expiratory flow (MEF).

In accordance with an embodiment, the index is analyzed and selected based on a group comprising:
maximal inspiratory pressure (MIP),
maximal expiratory pressure (MEP),
maximal inspiratory flow (MIF), and
maximal expiratory flow (MEF).

The exposure of the hyperthermia can be controlled and monitored by
using sensors, which measure a flow and a temperature at least from the inhaled airflow, preferably from the inhaled and the exhaled airflows,
calculating a value, i.e., the first and/or the second index, from the outputs of the said sensors, and
adjusting an optimal temperature, airflow resistance and/or respiratory time based on the calculated index.

Thus, the aspects of the disclosed embodiments relate to a measuring process, a data collection, a transition, and analysis methods for e.g. respiratory healthcare, wellbeing care, and/or sport performance services.

The device according to the aspects of the disclosed embodiments can comprise
a first flow channel for inhalation;
a body part comprising an inner volume, wherein a first space of the inner volume is adapted to be filled with liquid,
a second space of the inner volume being arranged to receive steam forming in the first space of the inner volume, whereby the first flow channel is arranged in a flow connection with the second space of the inner volume;
means for conveying a gas flow from the steam space of the inner volume via the first flow channel to the outside of the device during inhalation;
a second flow channel arranged in a flow connection with the first space of the inner volume adapted to provide exhaled air into the liquid;
means for conveying the exhaled gas flow from the outside of the device via the second flow channel to the first space of the inner volume to increase pressure in the inner volume,
means for measuring a flow and a temperature of an airflow, and
means for adjusting the flow of the airflow mechanically and/or automatically.

The aspects of the disclosed embodiments also relate to a method and a system.

A method according to the aspects of the disclosed embodiments can comprise the following steps:
conveying exhaled air via a second flow channel of a device to a first space of a body part of the device filled with liquid,
forming steam in the first space due to the exhaled air;
receiving in a second space of the body part of the device steam formed in the first space;
conveying a gas flow from the second space a first flow channel to the outside of the device during inhalation;
measuring flow and temperature of at least one of the inhaled airflow and exhaled airflow, and
adjusting flow resistance of at least one of the first flow channel and the second flow channel.

The device and the method according to the aspects of the disclosed embodiments are useful in adding breathing power and caring mucus membranes of the airways. Therefore, it adds respiratory wellbeing and helps to resist respiratory diseases. Using the device in parallel with the inhalable drugs, it is possible to reduce consumption of drugs because the device, according to the aspects of the disclosed embodiments, opens airways and allows the drugs to penetrate deeper into the airways than without the device.

The system according to the aspects of the disclosed embodiments can comprise the device comprising:
a first flow channel for inhalation;
a body part comprising an inner volume, wherein a first space of the inner volume is adapted to be filled with liquid,
a second space of the inner volume being arranged to receive steam forming in the first space of the inner volume, whereby the first flow channel is arranged in a flow connection with the second space of the inner volume;
means for conveying a gas flow from the steam space of the inner volume via the first flow channel to the outside of the device during inhalation;
a second flow channel arranged in a flow connection with the first space of the inner volume adapted to provide exhaled air into the liquid;
means for conveying the exhaled gas flow from the outside of the device via the second flow channel to the first space of the inner volume to increase pressure in the inner volume
optionally a local display,
measurement means for measuring a flow and a temperature of an inhaled airflow, and
optionally, measurement means for measuring a flow and a temperature of an exhaled airflow, and
optionally, a first valve, and a second valve.

The system according to the aspects of the disclosed embodiments can further comprise:
an integrated pressure and airflow monitoring and control unit comprising
a wireless component,
a processor, and
at least one memory component.

On inhalation, diaphragm and outer costal muscles contract causing negative thoracic pressure and airflow into the lungs. On exhalation, the inter costal muscles and diaphragm relax and the inner costal muscles contract causing positive thoracic pressure and airflow out of the lungs.

The device, according to the aspects of the disclosed embodiments, is also useful in leveraging respiratory functions of children and the aging. Along with aging, breathing capacity decreases due to many reasons such as stiffening of the rib case and shallow breathing. The asthmatic children are keen to limit their physical activity because of the breathing difficulties. This exposes them to the downward circle in which less activity leads to even poorer respiration The device according to the aspects of the disclose embodiments is especially useful in mucus clearance because the counter pressure on exhaling opens small bronchial tubes and generates pressure gradient which rises phlegm up from the lungs.

In an advantageous embodiment of the present disclosure, the exhaled air goes through a breathing resistance regulator into a water space. The airflow makes bubbles in the water space which increases area of the water surface and generates steam which rises on the top of the water space. On inhalation, the air in the water space goes through a check valve and breathing resistance regulator into lungs. The check valves in the air channels control the direction of the airflow and prevent the water to rise from the water space. In an advantageous embodiment of the present disclosure, the device has a vent hole which allows air flowing in and out of the device. On exhalation, the vent hole passes excess air out of the device, and on inhalation, it passes air inside the device. This air is mixed with the steam/air on the top of the water space. In advantageous embodiment of the present disclosure, chemicals such as drugs can be added into the water space or inhaling channel where they drift along with the airflow into lungs.

In accordance with an embodiment, at least a flow and a temperature of the inhaled air are measured, and an index based on said measurements is calculated. The index can be used for optimizing hyperthermia in airways.

The index can be selected based on a source data group comprising:
  calculated amount of energy gained during the inhaling,
  calculated amount of energy used during the exhaling,
  tidal volume (TV),
  inspiratory reserve volume (IRV),
  expiratory reserve volume (ERV),
  residual volume (RV),
  Lung Total Capacity
  maximal inspiratory pressure (MIP),
  maximal expiratory pressure (MEP),
  maximal inspiratory flow (MIF), and/or
  maximal expiratory flow (MEF).

In accordance with an embodiment, the calculated index is selected based on a group comprising:
  maximal inspiratory pressure (MIP),
  maximal expiratory pressure (MEP),
  maximal inspiratory flow (MIF), and/or
  maximal expiratory flow (MEF).

The drug added into the inhale air channel is carried immediately into the lungs on inhaled air, whereas the substances added into the water space vaporise into the top of the water space from where they are carried into the lungs on inhaled air.

Exhaling against resistance increases thoracic pressure which opens small bronchial tubes because the pressure is greater in the lower parts of the lungs. The mucus, accumulated in the lower bronchial tubes, drifts toward lower pressure i.e. larger tubes and finally out of the body by coughing. This phenomenon is attenuated by the inhaled steam which makes the phlegm more fluid and thus easier to be coughed out.

In accordance with an embodiment, at least a flow and a temperature of the exhaled airflow are measured, and an index based on said measurements is calculated. The index can be used for monitoring hyperthermia in airways. The index can be selected based on the source data group comprising:
  calculated amount of energy gained during the inhaling,
  calculated amount of energy used during the exhaling,
  tidal volume (TV),
  inspiratory reserve volume (IRV),
  expiratory reserve volume (ERV),
  residual volume (RV),
  Lung Total Capacity
  Heart rate variation
  maximal inspiratory pressure (MIP),
  maximal expiratory pressure (MEP),
  maximal inspiratory flow (MIF), and/or
  maximal expiratory flow (MEF).

In accordance with an embodiment, the calculated index is selected based on a group comprising:
  maximal inspiratory pressure (MIP),
  maximal expiratory pressure (MEP),
  maximal inspiratory flow (MIF), and/or
  maximal expiratory flow (MEF).

Since the device clears mucus from the airways, it reduces the risk of pneumonia especially for those who suffer from accumulation of mucus into the airways. It is also known that the device adds elasticity of the rib case by stretching the muscles and tissues around thorax. This improves breathing by allowing air to go deep into the lungs. The inhaled steam works in synergy with the increased thoracic pressure in mucus clearance from the airways.

In accordance with an embodiment, the airflow in inhale and exhale channels can be measured with sensor(s). The signals obtained are transmitted to a data processing system such as a mobile phone which can store and analyse the signals and transform them to information. This information is useful in motivating, monitoring, and advising the user. The information can be transmitted via a data processor to data pools such as health libraries.

DESCRIPTION OF THE DRAWINGS

In the following, the aspects of the disclosed embodiments will be described in more detail with reference to the appended drawings, in which.

DETAILED DESCRIPTION

The following reference numbers are used in this application:
1 a device,
2 a body part of the device, having a bottom 2a,
3 a liquid space,
4 a steam space
5 a first flow channel,
5a, 5b and end of the first flow channel,
6 a first valve,
7 a second flow channel, 7a, 7b an end of the second flow channel,
8 a second valve,
9 a third flow channel,
10 a mouthpiece,
11 liquid heating means,
12 a lid part,
13 a liquid space,
14 pressurizing means,
14a a piston,
14b a rod,
15 a transparent section,
16 electric energy transmission means,
17 a base,
18 a broken line illustrating a liquid level,
19 a replacement air valve,
21 a first sensor,
22 a second sensor,
24 a power supply,
25 a processor,
26 a memory component,
27 a display,
28 transmitting means,
29 adjusting means,
30 a respiratory cloud service unit, and
31 a controlling apparatus.

Figure 1:
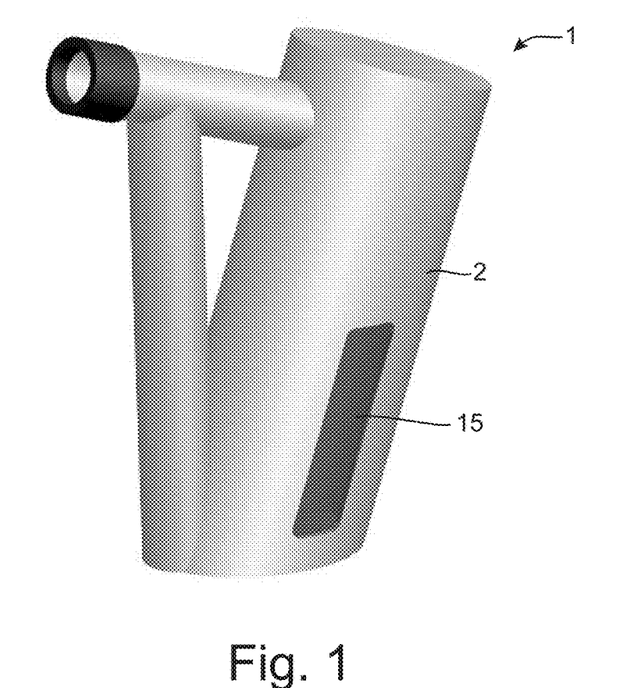
FIG. 1 shows a device according to an advantageous embodiment of the present disclosure in a perspective view.
Figure 2:
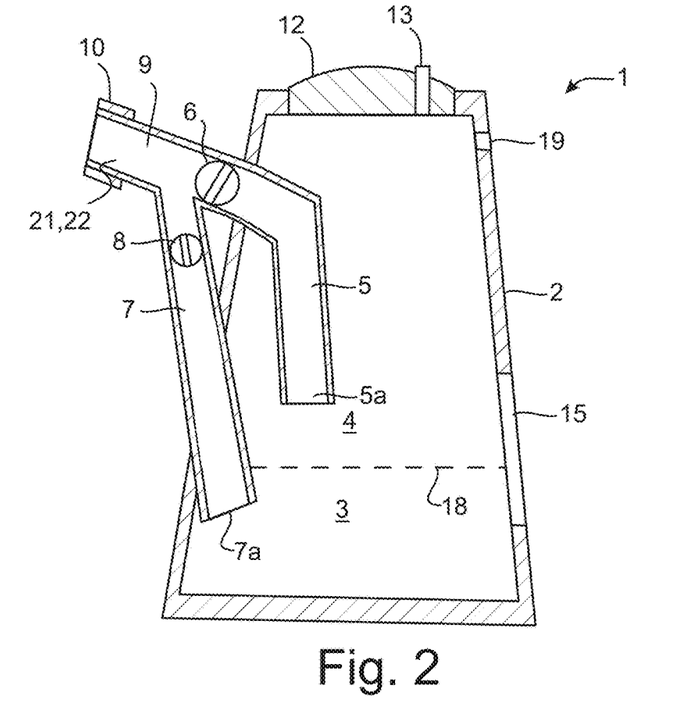
FIG. 2 shows a device according to the embodiment of FIG. 1 in a reduced cross-sectional view.

FIG. 1 shows a perspective view of a device 1 according to an advantageous embodiment of the present disclosure, and FIG. 2 shows the device of FIG. 1 in a reduced cross-sectional view. The device 1 comprises a body part 2 whose inner volume is provided with a liquid space 3 for a liquid, such as water. The body part 2 is advantageously thermally insulated either in part or in whole, to prevent the user from direct heat contact as well as to maintain the temperature of the water or liquid. Above in the liquid space 3, a steam space 4 detains the steam which rises from the liquid space. A flow channel 5 conveys the air from the steam space 4 into a user of the device 1. A check valve 6 controls the airflow direction in the air flow channel 5 allowing the air flow from the steam space 4 into the user but not vice versa. An end of the airflow channel 5a is placed above the liquid space 3 so that it will not be immerged in the liquid space 3.

Volume of the liquid space 3 and the steam space 4 may vary with the volume of the liquid added into the liquid space 3. The liquid space 3 is a volume of liquid such as water, and the steam space is a volume of steam such as molecular water vapour. Part of the outer body layer 2 can be transparent to allow visual detection of a liquid level 18 in the liquid space 3. It may also be equipped with a temperature display and device to help the user to follow the temperature of the liquid or/and steam.

The device 1 can also be provided with a lid part 12, through which liquid, such as water, can be supplied into the liquid space 3. The lid part 12 can be fastened relatively tightly to the body part 2 so that a sufficient pressure and temperature level can be maintained inside the body part during the use of the device 1.

The body part 2 has a vent hole 19 which allows the air flowing in and out during use of the device. The body part 2 or the lid part 12 is preferably provided with a replacement air valve 19, through which replacement air can be supplied into the inner volume of the body part at the inhalation step.

The device 1 has also an air channel 7 and a check valve 8 which allows the air to be blown into the liquid space 3. The check valve 8 blocks the airflow and liquid flow from the liquid space into the user. The end of the air channel 7a is placed beneath the liquid surface 18 in the liquid space 3.

The device 1 has also an air channel 9 which is connected to the air channels 5 and 7, and to a mouth piece 10. The mouth piece 10 can be a separate attachable part or integrated directly to the air channel 9.

In some cases, the mouthpiece 10 can be replaceable, wherein persons using the device can each have their own mouthpiece 10.

The device has a breathing regulator attached or integrated in the air channel 9. The breathing regulator works as an air flow resistor on in- and exhaling. The breathing regulator can be adjustable so that the resistance on ex- and inhaling can be chosen by the user.

The breathing regulator can be implemented in both airflow channels 5 and 7 separately. The breathing regulator works by narrowing the airflow channel thereby increasing breathing resistance on ex- and inhaling.

In accordance with an embodiment, flow of the inhaled airflow, steam and a temperature of said inhaled airflow are measured. Therefore, the device 1 preferably comprises a first sensor 21, i.e., a flow sensor, to measure the air or/and steam flow of the inhaled airflow and a second sensor 22, i.e., a temperature sensor, to measure the temperature of said inhaled airflow. The first sensor 21 and the second sensor 22 are preferably placed in connection with the third flow channel 9. The first sensor 21 and/or the second sensor 22 can also be movable sensors, i.e., the place of the sensor(s) 21, 22 can be determined according to the current need. For example, the sensor(s) 21, 22 can be movable placed in connection with the first flow channel 5, the second flow channel 7, and/or the third flow channel 9.

Further, flow of the exhaled airflow and temperature of said exhaled airflow can also be measured. The first sensor 21, i.e., a flow sensor, can be used to measure the flow of the exhaled airflow. The second sensor 22, i.e., a temperature sensor, can be used to measure the temperature of said exhaled airflow.

The first sensor 21 and the second sensor 22 can be placed in connection with the third flow channel 9 or the mouthpiece 10. Therefore, only one first sensor 21 may be needed to measure flow from both inhaled airflows and exhaled airflows. Further, only one second sensor 22 may be needed to measure temperature from both inhaled airflows and exhaled airflows. This may decrease manufacturing costs of the device 1 having the sensor(s) 21, 22.

In accordance with an embodiment, both the first flow channel 5 and the second flow channel 7 can have own flow sensor and/or temperature sensor. This may help the analysing process of measured parameters, because there is no need to determine whether the measurement parameters are from inhaled gases or exhaled gases.

With the absence of steam, typically, the exhaled air is warmer, has higher humidity and contains more $CO_2$ than the inhaled air. These variations can be used for indicating the respiratory rate. The airflow temperature and its fluctuation can also be used to adjust the most suitable airflow temperature of the device 1 for a user.

An airflow can be detected, for example, based on the airflow temperature or pressure. In the case of temperature-based airflow detection, there may not be a need for a separate flow sensor 21. Thus, costs may be decreased. On the other hand, this may not be very accurate method, hence, advantageously the device comprises a separate flow sensor 21 for measurements of an airflow, which flow sensor 21 is attached to the airways 5, 7, 9 of the device 1.

Thus, the device 1 preferably comprises a sensor 21 for flow measurements of inhaled and/or exhaled airflows, which sensor is attached to the airways of the device 1. The airflow(s) can be measured by using at least one of the following sensors:
- an airflow sensor,
- nasal or oronasal thermistor,
- nasal pressure transducer, or
- $CO_2$ sensor.

A first index (ix) is preferably calculated from said flow and temperature measurements coming from the sensors 21, 22. The first index (ix) can be used for optimizing hyperthermia in airways of an individual. The first index (ix) is, in other words, a value calculated from the outputs of the sensors 21, 22 and can be used for adjusting the optimal temperature and airflow resistance and, preferably, also the optimal respiratory time for the individual. When determining the optimal temperature, airflow resistance and/or respiratory time, previously obtained measurements can be used as a reference value for the adjusting process.

In other words, at least a respiratory time, such as 5 to 15 s., and a temperature of the inhaled airflow, preferably also a flow of the inhaled airflow, are measured and one, two or more indices based on said measurements is calculated.

The calculated index or indices can be used for optimizing hyperthermia in airways. In accordance with an embodiment, a first index is a value of thermal exposure and it can be calculated from inhaling airflows, and a second index can be calculated from exhaling airflows.

The at least one index can be selected based on the source date comprising:
- calculated amount of energy gained during the inhaling,
- calculated amount of energy used during the exhaling,
- tidal volume (TV),
- inspiratory reserve volume (IRV),
- expiratory reserve volume (ERV),
- residual volume (RV),
- Lung Total Capacity (LTC),
- Heart Rate Variation
- maximal inspiratory pressure (MIP),
- maximal expiratory pressure (MEP),
- maximal inspiratory flow (MIF), and/or
- maximal expiratory flow (MEF).

In accordance with an embodiment, the calculated index is selected based on a group comprising:
- maximal inspiratory pressure (MIP),
- maximal expiratory pressure (MEP),
- maximal inspiratory flow (MIF), and/or
- maximal expiratory flow (MEF).

In accordance with an embodiment, the first index is calculated as a function of at least total inhaling time (tINtot) and a temperature (TIN) of the inhaled air. Total inhaling time (tINtot) is a time used for predetermined number of inhaling times tIN1-tINn, i.e., sum of time for the predetermined number of inhalings. Calculated temperature (TavmaxIN) of the inhaled airflow is an average of the maximal measured temperatures TmaxIN of the TIN1-TINn.

Therefore, the first index can be calculated from the following equation:

$$\text{first index} = \text{TavmaxIN} \times \text{tINtot}.$$

The first index can illustrate the energy transferred into the airways by the steam. The first index can be useful when estimating a level of hyperthermia in the upper airways.

The second index can be calculated as a function of at least total exhaling time (tEXtot) and temperature of the exhaled air (TEX). Total exhaling time (tEXtot) is a time used for predetermined number of exhaling times tEX1-tEXn, i.e., a sum of time for the predetermined number of exhalings. Calculated temperature (TavmaxEX) of the exhaled airflow is an average of the maximal measured temperatures TmaxEX of the TEX1-TEXn.

Thus, the second index can be calculated from the equation:

$$\text{second index} = \text{TavmaxEX} \times \text{tEXtot}.$$

The second index illustrates the energy transferred from the airways. The second index can be useful, especially, when used together with the first index.

In order to achieve more accurate first index representing the total inhaled energy, the total inhaled air volume can be determined. This can be calculated based on the measured airflow and time used for one inhaling.

Thus, the first index is preferably determined by
- measuring a flow of the inhaled airflow,
- measuring a temperature of the inhaled airflow,
- determining a time of the inhaled airflow,
- calculating a total volume by using the inhaled airflow and the time used for said inhaled airflow,
- determining a water vapour density from the temperature of the inhaled airflow,
- calculating an amount of the water in the airflow by using the water vapour density and the calculated total volume,
- determining water vapour specific heat capacity in the measured temperature, and/or
- calculating the amount of energy gained during the inhaling based on the measurements and analysis, i.e., based on the heat capacity, the amount of the water in the airflow, and the time.

The following example illustrates how the index can be calculated:

The measurements show that a flow of an inhaled airflow of an individual is 10 l/min and temperature of the airflow is 60° C. Further, an inhaling time of the individual is 10 s. Thus, the total volume calculated from the airflow and the time is 10 l/min*⅙ min is about 1.67 l. The temperature is 60° C. and the vapour density can be determined based on the temperature (130.5 mg/l at 60° C.), hence, the amount of water can be calculated. Taking into account the water vapour specific heat capacity, 2.0 J/g energy, the maximum amount of energy that is gained during single round breathing is 0.783 J. Thus, with the inhaling time of said 10 s., the total amount of energy for the set airflow and for the inhaling period is 7.83 J.

When the total amount of energy is calculated, for example a temperature of the inhaled airflow, a time used for the inhaling and/or exhaling, and/or a flow resistance of the exhaling and/or inhaling can be adjusted in order to obtain the predetermined amount of energy. Thus, preferably the method comprises adjusting at least a temperature of the inhaled airflow, a time used for the inhaling, and/or a flow resistance for inhaling in order to obtain the predetermined amount of energy.

In order to achieve accurate second index representing the total exhaled energy, also the total exhaled air volume can be calculated. This can be calculated based on the measured airflow and the time used for one exhaling.

Thus, the second index is preferably calculated by measuring a flow of the exhaled airflow, measuring a temperature of the exhaled airflow, determining a time of the exhaled airflow, calculating total volume by using the exhaled airflow and the time of said exhaled airflow, determining vapour density from the temperature of the exhaled airflow, calculating an amount of the water using the vapour density and the total volume, determining water vapour specific heat capacity in said temperature, calculating the amount of energy during the exhaling based on said heat capacity, the amount of the water in the airflow, and the time.

The method can further comprise adjusting a temperature of the inhaled airflow, optionally adjusting time used for the inhaling, optionally adjusting a time used for the exhaling, adjusting a flow resistance for the exhaling, and adjusting a flow resistance for inhaling in order to obtain the predetermined amount of energy.

At least a temperature of the inhaled airflow is preferably adjusted. In addition, at least a flow resistance for exhaling is preferably adjusted. In addition, at least a flow resistance for inhaling is preferably adjusted.

In accordance with an embodiment, the first index and the second index can be calculated based on
- the Tidal Volume (TV), which represents the amount of air that can be inhaled and exhaled during one normal (quiet) breathing cycle,
- Inspiratory Reserve Volume (IRV), which represents the amount of air that can be forcibly inhaled beyond a tidal inhalation, and
- Expiratory Reserve Volume (ERV), which represents the amount of air that can be forcibly exhaled beyond a tidal exhalation,
- monitoring during the airway monitoring and adjusting process.

In addition, Residual Volume (RV), which represents the amount of air remaining in the lungs after an ERV, and Lung Total Capacity (LTC) (a.k.a., Respiratory capacities, lung capacity, functional reverse capacity, vital capacity, total lung capacity) can be used for the calculation of the first index and/or the second index.

The Tidal Volume can be calculated by using flow measurements of the inhaled and/or exhaled airflows and time used for the inhaling and/or exhaling, which measurements are taken during normal breathing cycle.

Inspiratory Reserve Volume can be calculated when a flow of the inhaled airflow and a time of the inhaled airflow are measured when air is forcibly inhaled, and the Tidal Volume is known.

Expiratory Reserve Volume can be calculated when a flow of the exhaled airflow and a time of the exhaled airflow are measured when air is forcibly exhaled, and the Tidal Volume is known.

Residual Volume can be calculated when the Expiratory Reserve Volume and the Lung Total Capacity are determined.

Figure 8A:
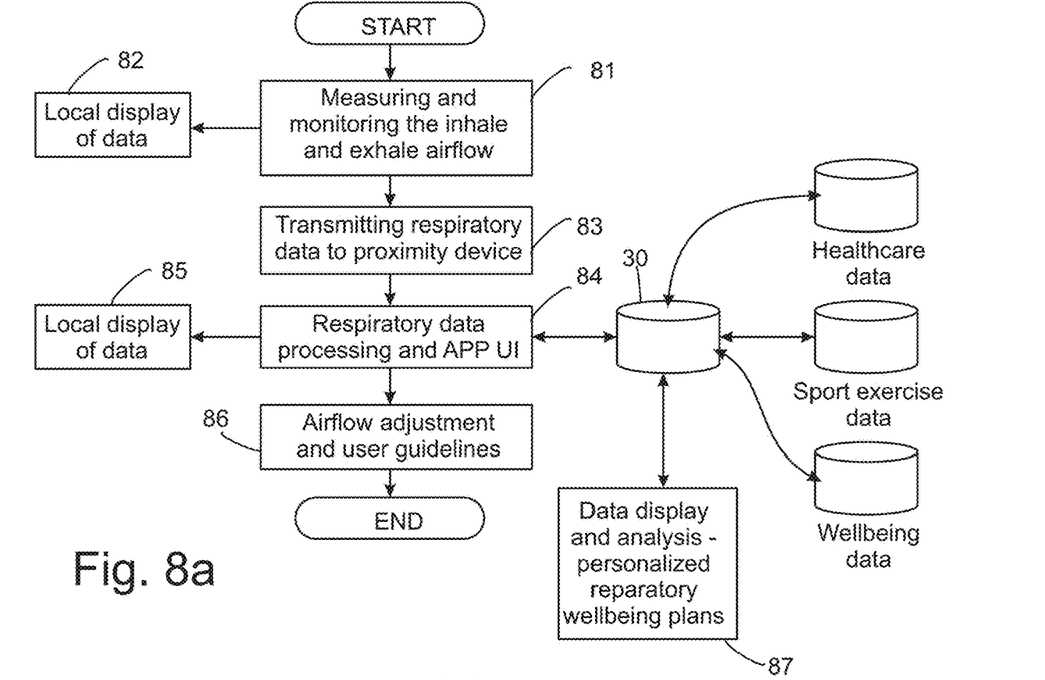
FIG. 8a shows an example of a method for a system, in accordance with an embodiment.
Figure 8B:
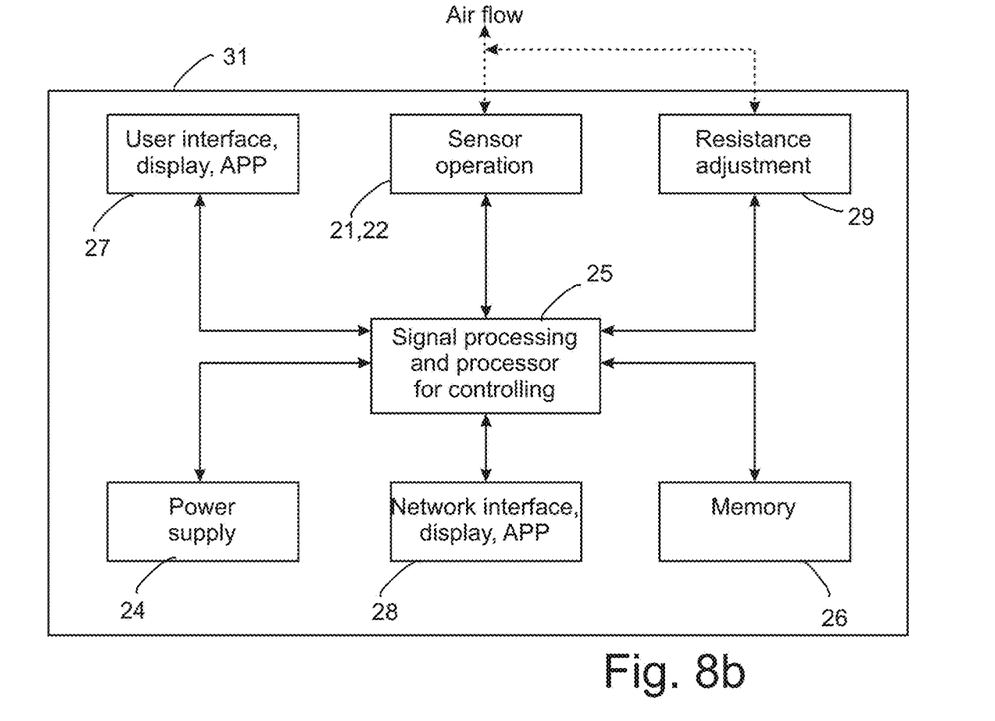
FIG. 8b shows as a simplified block diagram an example of a controlling apparatus, in accordance with an embodiment.

In accordance with an embodiment, the device 1 further comprises means for transferring measurement results (the outputs of the sensors 21, 22) to, for example, a controlling apparatus 31 an example of which is depicted in FIG. 8b as a simplified block diagram. The controlling apparatus 31 comprises a processor 25, a memory 26 for storing data and computer code to be executed by the processor 25, a user interface 27 having, for example, a display and a keyboard (not shown in the Figures). The controlling apparatus 31 further comprises a sensor interface for receiving the outputs from the sensors 21, 22, and an adjustment element 29 for adjusting resistance and/or temperature. There is also a power supply 24 for supplying power for the operation of the controlling apparatus 31. For communication purposes the controlling apparatus 31 may be equipped with a communication interface 28, which may be able to communicate with some other devices, e.g. a cloud service unit 31, via short range and/or long range communication connection.

The processor 25 can be used to analyse the measurements obtained from the sensors 21, 22 in order to adjust flow resistance and temperature of inhaled and/or exhaled airflow and, optionally, respiratory time.

Thus, an exposure of a hyperthermia can at least be monitored, for example by using the sensor(s) 21, 22, which measure at least the airflow and the temperature of the inhaled and/or exhaled air. In accordance with an embodiment, the exposure of the hyperthermia is not only monitored but also adjusted to improve respiratory functions.

The device 1 can comprise at least
- means for measuring a flow of an inhaled airflow and/or an exhaled airflow, such as the sensor 21, and
- means for measuring a temperature of the inhaled airflow and/or exhaled airflow, such as the sensor 22,
- means for adjusting flow resistance of at least one of the first flow channel 5 and the second flow channel 7.

A system (shown in FIGS. 8a-8b) preferably comprises at least the device 1, the controlling apparatus 31, and at least one sensor 21, 22 for measurements.

In accordance with an embodiment, the respiratory cloud service unit 30 may be a part of the system.

In accordance with an embodiment, the system comprises means for collecting data from the above-mentioned temperature and/or flow measurements, means for analysing the collected data to form a first index (ix), which first index (ix) is calculated by using the above-mentioned measurements, adjusting means 29 for adjusting the flow resistance and/or the temperature of the airflow, and means for determining a respiratory time, such as 8-10 s.

The system may also comprise means for analysing the collected data to form a second index (id), which second index is calculated by using the above-mentioned measurements from the exhaling airflows.

The system may further comprise means for analysing the collected data to form a third index, and/or a fourth index, which are values calculated by using the above-mentioned measurements.

In accordance with an embodiment, every index is selected based on the following source data group:
- calculated amount of energy gained during the inhaling,
- calculated amount of energy used during the exhaling,
- tidal volume (TV),
- inspiratory reserve volume (IRV),
- expiratory reserve volume (ERV),
- residual volume (RV),
- Lung Total Capacity (LTC),
- Heart rate variation,
- maximal inspiratory pressure (MIP),
- maximal expiratory pressure (MEP),
- maximal inspiratory flow (MIF), and/or
- maximal expiratory flow (MEF).

Preferably, every index is selected based on the following group:
- calculated amount of energy gained during the inhaling, and/or
- calculated amount of energy used during the exhaling,
- maximal inspiratory pressure (MIP),
- maximal expiratory pressure (MEP),
- maximal inspiratory flow (MIF), and/or
- maximal expiratory flow (MEF).

Most preferably, every index is selected based on the following group:
- calculated amount of energy gained during the inhaling, and/or
- calculated amount of energy used during the exhaling.

Thus, the system comprising the device 1 can comprise means for calculating at least one index, such as:

means for calculating an amount of energy gained during the inhaling,
means for calculating an amount of energy transferred during the exhaling,
means for calculating tidal volume (TV),
means for calculating inspiratory reserve volume (IRV),
means for calculating expiratory reserve volume (ERV),
means for calculating residual volume (RV),
means for calculating Lung Total Capacity (LTC),
means for calculating the heart rate variation,
means for calculating a maximal inspiratory pressure (MIP) of an individual, and
means for calculating a maximal expiratory pressure (MEP) of an individual,
means for calculating a maximal inspiratory flow (MIF) of an individual, and/or
means for calculating the maximal expiratory flow (MEF) of an individual.

Means for calculating at least one index can comprise at least a processor 25.

These values can be used to help the individual, i.e. the user of the device, to adjust an airflow resistance with adjusting means 29 by adjusting the flow resistance of an adjustable flow throttling device, such as the first valve 6 and/or the second valve 8. In accordance with an embodiment, the adjustment is performed with adjusting means 29 manually by the guided user via display 27 or automatically, for example under the control of the processor 25 or on the basis of adjustment information received from a remote location, e.g. from a respiratory cloud service unit 30 or a software application and based on predefined step sizes in the device or/and in the User Interface. The adjustment of the flow resistance with the adjusting means 29 may be implemented, for example, by controlling a position of at least one valve 6, 8 of the device 1.

In accordance with an embodiment, at least some of data coming from the measurements are stored and analyzed in the device 1 and/or the respiratory cloud service unit 30. Advantageously at least history data of calculated amount of energy gained during the inhaling, calculated amount of energy used during the exhaling, maximal inspiratory pressure, maximal expiratory pressure, maximal inspiratory flow, and/or maximal expiratory flow is used to define a user airflow resistance profile. Further, a proposed airflow resistance (a recommended valve position in the device 1) can be recommended for the user based on the measured (history) data and a reference data. This is defined, for example, based on the total lung volume data vs. the resistance used by the user during the exercise period.

In accordance with an embodiment, data showing the recommended airflow resistance is stored in the memory component 26 of the processor unit and displayed on a display 27, for example, on a display 27 of the device 1. In addition, the data showing the recommended airflow resistance can be used in a software application and/or in the cloud service database for the respiratory training program use. By using the recommended data, an individual (i.e., a user) can select, for example, the most appropriate airflow resistance.

An airflow resistance can be adjusted mechanically/manually with adjusting means 29. It can be adjusted mechanically, for example, by using a peripheral adjuster, and automatically, for example, by selecting the option in a user interface of the software application.

Furthermore, the measurement such as measurements of maximal inspiratory pressure MIP and the maximal expiratory pressure MEP can be used to assess muscle pressures of the user. Moreover, for example said MIP and MEP-values may be very useful in the diagnosis and follow-up of pulmonary and cardiac disease. In addition, an imbalance between the pressure generated by the inspiratory muscles and the MIP-value may lead to the development of hypercapnia in patients with chronic obstructive pulmonary diseases (COPD).

Thus, especially MIP and MEP may be very useful in predicting the post-operative pulmonary complications following coronary artery by-pass graft surgery. An imbalance between respiratory mechanical load and respiratory muscle capability may also be a cause of difficulty when weaning the patients from mechanical ventilation. Likewise, MIP may be a very sensitive predictive value of successful weaning.

The method can comprise the following steps:
measuring a flow and a temperature of an inhaled airflow, wherein measurements are implemented by using at least one sensor 21, 22,
optionally, determining a time of the inhaled airflow,
collecting data from the inhaled airflow(s) measurements,
analysing the collected data in order to form a first index (ix), which first index (ix) is calculated by using the above-mentioned measurements from the inhaled airflows, and
adjusting at least one of the following parameters by using said first index (ix), preferably adjusting all of the following parameters:
flow resistance of the inhaled airflow,
flow resistance of the exhaled airflow, and
temperature of the inhaled airflow.

In accordance with an embodiment, the method further comprises:
measuring an exhaled airflow, and a temperature of the exhaled airflow,
determining a time of the exhaled airflow,
collecting a data from the exhaled airflows measurements, analysing the collected data, optionally together with the data of the inhaled airflow(s) measurements, in order to form a second index (id) which second index (id) is calculated by using at least the above-mentioned measurements from the exhaled airflows,
adjusting at least one of the following parameters, preferably all of the following parameters, by using said second index (id) and optionally also the first index (ix):
optionally, time of the inhaled airflow,
flow resistance of the inhaled airflow,
flow resistance of the exhaled airflow,
temperature of the inhaled airflow, and
optionally, the time of the exhaled airflow.

In accordance with an embodiment, the method comprises:
measuring pressure of the inhaling airflow,
measuring pressure of the exhaling airflow,
measuring flow of the inhaling airflow,
measuring flow of the exhaling airflow,
calculating
maximal inspiratory pressure MIP,
maximal expiratory pressure MEP,
maximal inspiratory flow MIF, and/or
maximal expiratory flow MEF, and
using at least one of the calculated values as the first index and/or the second index.

Thanks to the above-mentioned measurements, analysis and adjustments, it is possible, among other mentioned things, to help a user to adjust the airflow resistance and choose his/her personalized training program.

Figures 3A, 3B, 4, 5:
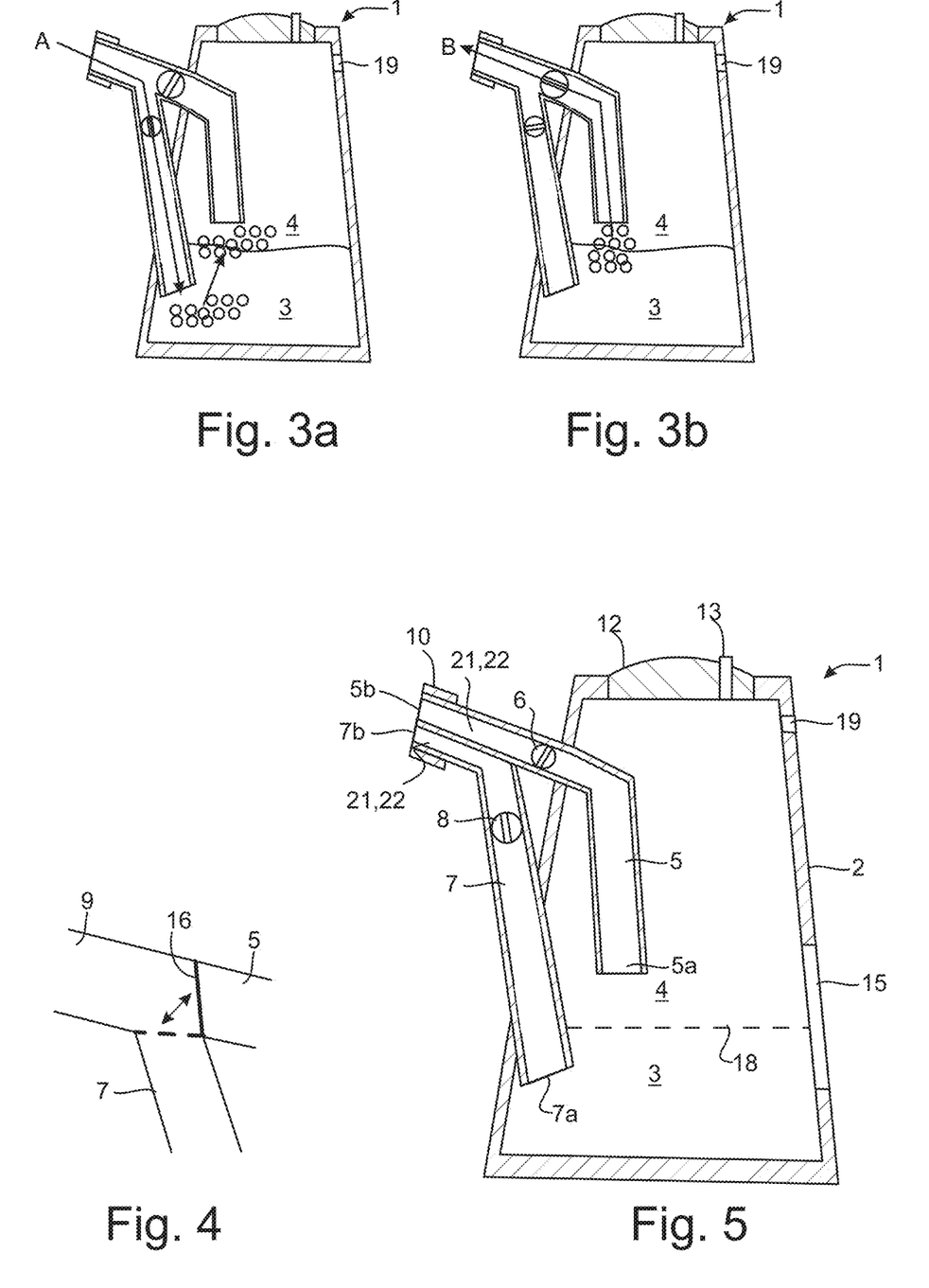
FIGS. 3a and 3b show the function of flow channels in different breathing steps in principle views.
FIG. 4 shows an alternative valve arrangement for guiding air flows in the different functional steps of the device.
FIG. 5 shows an alternative arrangement of flow channels in the device.

In the following, the operation of the device according to FIG. 1 will be described in a care situation with reference to FIGS. 3a and 3b. The liquid space 3 of the device is filled with a liquid, such as water, to a given height level. This height level is advantageously such that one end 5a of the first flow channel 5 is above the liquid level, but one end 7a of the second liquid channel 7 is below the surface of the liquid. The liquid to be supplied to the liquid space is preferably heated, for example by a separate heating device, or warm water is supplied into the liquid space from the hot water tap of a building, or the like. The target temperature of the liquid may vary in different situations, but it has been found that in the care of respiratory diseases, the temperature of the liquid should not be boiling but, for example, 60 to 70 degrees at the most, or even cooler. Thus, if the temperature of the liquid rises higher than the target temperature at the heating stage, there may be a need to allow the liquid to cool down before the device 1 is used by the person to be cared for.

When the liquid space 3 has been filled with a suitable quantity of the liquid and the temperature of the liquid is suitable, the care measures can be started. The device includes a temperature display or other temperature monitoring means so that the user can follow the degree of the temperature before starting the exercise. The person to be cared for places the mouthpiece 10 in his/her mouth and starts to blow. Thus, the air from the subject's lungs flows into the third flow channel 9 and from there further to the second flow channel 7. In practice, air can flow into the first flow channel 5 as well, but the first valve 6 in the first flow channel is in a position that prevents the air from flowing further in the first flow channel 5. In other words, the first valve 6 prevents the air from flowing via the first flow channel 5 into the steam space 4. Instead, the second valve 8 in the second flow channel 7 is in a position that allows the exhaled air to flow into the liquid space 3. The liquid in this liquid space 3 causes a flow resistance which has the effect that the person has to blow harder so that the exhaled air can flow into the liquid space 3. This has been found to be useful in the care, because the muscles involved in the function of the lungs have to work harder, which also strengthens these muscles when the care is continued. Furthermore, the opening of the bronchial tubes is more effective, when a clearly resisting force effect is produced against the exhalation. The air flows of this step are illustrated with an arrow A in FIG. 3a.

In the liquid space 3, the exhalation has the effect that bubbles (pores) are formed in the liquid and the pressure inside the body part, e.g. in the liquid space 3, increases. As a result, part of the liquid in the liquid space 3 is evaporated and this steam rises to the steam space 4, although the temperature of the liquid is below the evaporating point of the liquid. If the liquid space 3 or the steam space 4 contains drug, the delivery of the drug with the inhaled steam into the lungs is enhanced as well. The exhalation is followed by an inhalation step which induces the following chain of operations in the device 1. When the person starts to inhale by drawing air through the mouthpiece 10 into his/her lungs, an underpressure is formed in both the first flow channel 5 and the second flow channel 7. Thus, the second valve in the second flow channel 7 is closed and prevents the flow of air through the second flow channel 7 into the lungs. Instead, the first valve 6 in the first flow channel 5 opens and lets air flow from the steam space 4 through the first flow channel 5 into the lungs. This inhaled air also entrains steam from the steam space 4; in other words, the device functions as a steam inhaler. The air flows of this step are illustrated with an arrow B in FIG. 3b. Because the inhalation step follows the exhalation step substantially immediately, the bronchial tubes do not have time to close, which is substantially effective and enhances the access to the lungs by steam and possible drugs contained in it. Both the blowing resistance and the inhalation resistance can be adjusted, because the lungs and the muscles supporting them are activated in the resisted inhalation as well.

In the above described step 1, the first valve 6 and the second valve 8 are automatically pressure-operated valves, kind of back-pressure valves, by which the guidance of the air flow can be operated in a controlled manner as desired. In the device 1, it is also possible to use other kinds of valves, by which the control of the air flow can be implemented by applying the above-mentioned principle. As an example, manually operated valves can be mentioned. The user him/herself or his/her assistant can adjust the valves according to the need; consequently, in the exhalation step, the flow through the first flow channel 5 is prevented, and in a corresponding manner in the inhalation step, the air flow through the second flow channel 7 is prevented. In an embodiment, the first valve 6 and the second valve 8 can be replaced by a single valve with a shutter (for example baffle 16, FIG. 4) which can alternately close the first flow channel 5 and the second flow channel 7. The control of the valves 6, 8 can also be implemented by automation, wherein a sensor or the like may be needed to detect if the person is breathing out or in and, on the basis of this, to control the operation of the valves 6, 8 in an appropriate way.

Further, at least some of the measurements, analysis and adjustments disclosed in this application are used in order to optimize hyperthermia in airways.

In the device 1 of FIG. 1, the first flow channel 5 and the second flow channel 7 are connected at one end 5b, 7b to a single flow channel, that is, the third flow channel 9. However, the device 1 according to the aspects of the disclosed embodiments can also be implemented in such a way that the third flow channel 9 is not needed but both the first flow channel 5 and the second flow channel 7 are led to the mouthpiece 10, whereby both the second end 5b of the first flow channel 5 and the second end 7b of the second flow channel 7 are in the mouthpiece and the person places these in his/her mouth for the time of using the device. Said second end 5b of the first flow channel 5 and the second end 7b of the second flow channel 7 are close to each other, advantageously in parallel, on top of or obliquely to each other in such a way that the second ends 5b, 7b of both flow channels fit in the subject's mouth simultaneously. One example of such an implementation is shown in FIG. 5.

Figure 6:
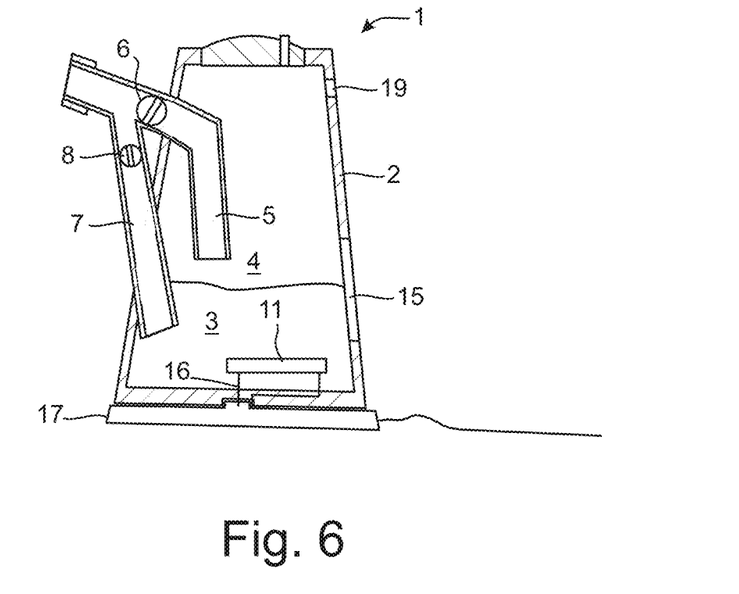
FIG. 6 shows a device according to another advantageous embodiment of the present disclosure in a reduced cross-sectional view.

In connection with the operation of the above-described device 1, it was mentioned that the liquid is heated outside the device 1, for example by a separate heater, such as a coffee maker, a kettle, or the like. The implementation can be done in such a way that the heating of the liquid is arranged in the device 1 itself, or the device 1 can be heated from the outside for heating the liquid in the liquid space 3 of the device. FIG. 6 shows a reduced cross-sectional view of a device 1 according to another embodiment, comprising liquid heating means 11 for heating the liquid. Thus, the heating of the liquid in the liquid space 3 can be performed by liquid heating means 11. The liquid heating means 11 can be implemented, for example, by means of a heating resistor, wherein electricity is conducted to the heating resistor for the time of heating. The electric energy needed for the heating can be conducted, for example, by electric energy transmission means 16 provided in the bottom 2a of the body part, or the device can be provided with a stationary electric wire which is connected e.g. to an electrical outlet or converter when heating is needed. If said electrical energy transmission means are provided at the bottom 2a of the device, the device 1 can be provided with a base 17 with corresponding means which can be connected either directly or inductively to the electric energy transmission means of the device. For a person skilled in the art, it is obvious how such electric energy transmission can be implemented in a wired or wireless manner, so a more detailed description of it in this context will not be necessary.

Advantageously, the device 1 also comprises a lid 12 which can be opened and/or removed, for example for filling the liquid space 3. The lid 12 or the body part 2 can also be provided with a relief valve 13 which may prevent the pressure from rising too much inside the device 1. The lid 12 can also be provided with an opening, through which drug or another substance can be supplied to the liquid in the liquid space. On the other hand, the inner volume of the device 1, for example the inner surface of the body part, can be provided with a container or the like, to which the drug can be supplied and from which the drug is gradually transferred to the liquid in the liquid space 3.

If the device 1 is provided with liquid heating means 11 of the above-mentioned type, it may also be necessary to provide the device 1 with control means (not shown in the appended drawings) for controlling the heating process, inter alia to avoid excessive heating. With the control means it is possible, for example, to control the temperature of the liquid, wherein it is possible to use liquids at different temperatures for different uses.

In an advantageous embodiment, the heating means 11 can also be used, among other things, for disinfecting the device. Thus, the liquid is heated to a higher temperature than in a care situation, for example to the boiling point (100 degrees). This will clean at least part of the impurities, wherein the use of the device 1 in care situations may be safer. During the disinfecting step, the use of the device for care is preferably prevented. This can be implemented, for example, in such a way that the first valve 6 and the second valve 8 are placed in a position which prevents the flow of air from the liquid space 3 and the steam space 4 to the mouthpiece 10.

The device 1 can also be washed with a dishwashing liquid either by hand or in a dishwasher, or ultrasonic cleaning or the like can be used.

In the following, we will briefly present some further heating methods. Applying them in practice may require that the requirements of the different heating methods are taken into account in the structure of the device 1, including for example the heat resistance. One possible heating method is to place the device on a heating element (for example, a hot plate of an electric stove), wherein the heat of the heating element is conducted through the bottom of the body part to the liquid in the liquid space 3. A heating method of a corresponding type is to use a campfire for heating the liquid. Yet another possibility may be to use a microwave oven, wherein the device 1 is placed in the microwave oven. Thus, the device 1 should not contain such materials which could hamper the operation of the microwave oven and which are hardly heated by microwaves at all. Some kinds of heating methods based on thermochemical phenomena or ultrasonic liquid atomizer may also be used. In this context, one should mention so-called heat cartridges which can be placed on the bottom of the device for heating. The heat cartridges can be based on using, for example, sodium acetate, iron dust, burnt lime, or aluminium chloride.

In some cases, the heating means of the device 1 can be driven by, for example, a battery, whereby the device can also be used in situations in which there is no separate source of electrical energy available.

The device 1 can also be provided with other automation and control for e.g. informing the user of the device about a possible need for maintenance, displaying the temperature of the liquid, etc.

In an advantageous embodiment, the device 1 is used for storing treatment sessions in a memory, so that it is possible to monitor the outcome of the treatments and to follow up on progress in the care. This may be useful, for example, for nursing staff who may use the data to make sure that the care has been taken in due course and appropriately.

Figure 7:
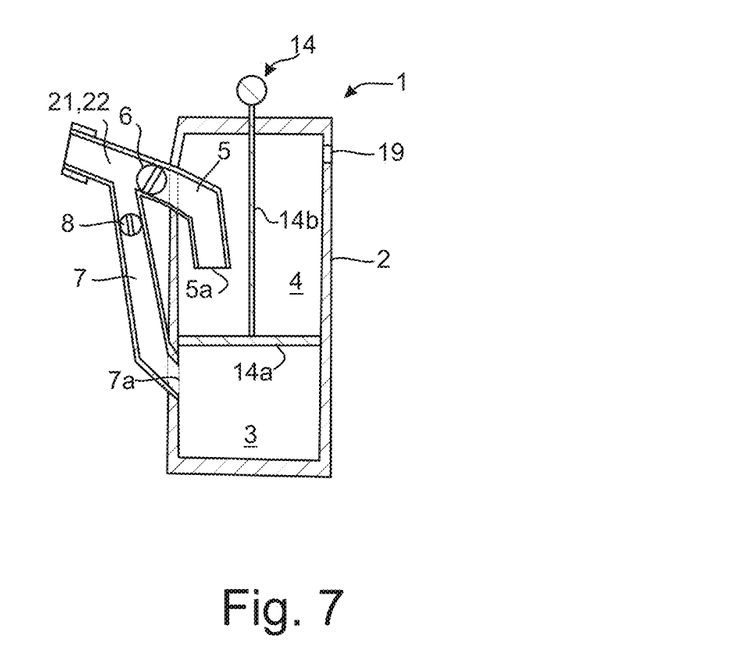
FIG. 7 shows a device according to yet a third advantageous embodiment of the present disclosure in a reduced cross-section.

FIG. 7 shows a reduced cross-sectional view of yet another advantageous embodiment of the device 1. It comprises pressurizing means 14 for increasing the pressure prevailing in the liquid space 3. This may be needed, for example, in situations in which the person to be cared for is not capable of blowing air sufficiently strongly into the device 1 during exhalation. The pressurizing means 14 comprise, for example, a piston 14a or the like which can move in the inner volume of the body part, for example towards the bottom part 2a and away from the bottom part 2a. This movement can be produced, for example, by pressing the rod 14b downwards or by lifting the rod 14b upwards. Because the pressure increase preferably has to be produced in the liquid in the liquid space 3, and steam forming in the liquid should still enter the steam space 4, the piston 14a is advantageously equipped with channels or the like, through which steam can rise to the steam space 4. Although the piston 14a is thus not fully sealed, the piston 14a can still be used for increasing the pressure in the liquid space 3. Such pressurizing means 14 can be employed by, for example, the user of the device or his/her aide. The required pressure level can be set according to the user's feelings, wherein it is possible to avoid applying too high a pressure.

In some embodiments, an external pressure source can be used, such as a compressor (not shown) for increasing the pressure in the liquid space 3.

Further, at least some of the measurements, analyses and adjustments disclosed in this application can be used in order to optimize hyperthermia in airways of an individual.

FIG. 8a shows an example of a method, and FIG. 8b shows an example of the system comprising the device 1.

In accordance with an embodiment, air/steam flow and temperature of the inhaled airflow is measured 81, and optionally, a time used for the inhaling is determined.

Further, in accordance with the embodiment, preferably flow and temperature of the exhaled airflow is measured, and optionally, a time used for the exhaling is determined.

Further, data from the above-mentioned measurements from inhaled airflows and/or exhaled airflows, preferably from both airflows, is collected, and optionally, the collected data, or at least some of the collected data, is shown 82 to a user using a local display 27.

Further, at least some of the collected data can be transmitted 83 with transmitting means 28 to a proximity device, where the transmitted respiratory data is processed 84, i.e., analysed. Optionally, the collected data is displayed 85 in a local display 27, and optionally, information of airflow resistance adjustment and/or user guidelines, based on the above disclosed measurements and analyses, is provided 86.

Further, at least some of the processed data can be transmitted with transmitting means 28 to a respiratory cloud service unit 30. It may also be possible that information of an airflow resistance adjustment and a user guideline is provided 87. The collected data may be displayed in a display 27 of the device 1.

The processed data can be used, for example, for healthcare (i.e., healthcare data), for sport exercise (i.e., sport exercise data), and/or for wellbeing (i.e., wellbeing data). For example, the processed data can be used along with the heart rate variation of the user to give the performance feedback to the user.

The analysing (processing) step, wherein the collected respiratory data is processed, can comprise at least the following steps. The collected data is analysed in order to form a first index (ix), which first index (ix) is calculated by using the above-mentioned measurements from the airflows. The airflow resistance is adjusted, for example by using said first index (ix), and the temperature of the airflow is adjusted, for example by using said first index (ix), and/or a respiratory time is adjusted.

In accordance with an embodiment, the first index is selected based on the source data group comprising:
calculated amount of energy gained during the inhaling,
calculated amount of energy used during the exhaling,
tidal volume (TV),
inspiratory reserve volume (IRV),
expiratory reserve volume (ERV),
residual volume (RV),
Lung Total Capacity
Heart rate variation
maximal inspiratory pressure (MIP),
maximal expiratory pressure (MEP),
maximal inspiratory flow (MIF), and/or
maximal expiratory flow (MEF).
the respiratory cloud service unit 30 (RCS) can store all or at least some of the following respiratory data:
the average of the maximal measured temperatures,
the total inhaling time,
the average of the maximal measured temperatures,
the calculated amount of energy gained during the inhaling,
the calculated amount of energy transferred during the exhaling,
the tidal volume (TV),
the inspiratory reserve volume (IRV),
the expiratory reserve volume (ERV),
the residual volume (RV),
Lung Total Capacity (LTC),
the maximal inspiratory pressure (MIP),
the maximal expiratory pressure (MEP),
the maximal inspiratory flow (MIF), and/or
the maximal expiratory flow (MEF).

Further, the respiratory cloud service unit 30 can also maintain history data, at least for a predetermined time. The respiratory cloud service unit 30 can also provide means to process and analysis said data.

The system can comprise
the device 1, and
an integrated pressure and airflow monitoring and control unit (PAM).

The integrated pressure and airflow monitoring and control unit (PAM) can comprise at least:
a wireless component,
a processor 25,
a power supply 24, and
at least one memory component 26.

The respiratory cloud service unit 30, the transmitting means 28 such as the wireless component, and receiving data can be based on
Radio Frequency Identification (RFID),
BT (Bluetooth),
Wireless Local Access Network (WLAN), or
Near Field Communication (NFC),
but it may alternatively be based on any other, preferably wireless, technologies.

The processor 25 used for processing data can be, for example, a processor of a mobile device, a tablet, or a personal computer (such as a laptop computer).

Furthermore, a respiratory application may be used to collect data, create biofeedback and/or monitor the related data. The respiratory application may use wide area network or fixed network to transmit the data using the transmitting means 28, for example, to the respiratory Cloud Computing Unit (CCU) of the respiratory cloud service unit 30. The User Interface (UI) of the software application may be used to offer the users instant respiratory feedback.

In accordance with an embodiment, the integrated pressure and airflow monitoring and control unit (PAM) comprises:
means for getting data from the inhale and/or exhale airflow, preferably from the both airflows,
a data storage,
a processor 25 for processing collected data,
a transmitting means 28, such as a component for transmitting and receiving data to/from the proximity wireless device or local network.

The airflow data transmission via a system, such as wireless system, can be performed in real time or replicated based on predefined time period. The data can be transmitted, for example, to a WLAN based station, mobile system Based Station (BS) or to the fixed network.

The respiratory cloud service unit 30 can be used to provide means to create personalized respiratory analysis, "tailor-made" training plans and/or healthcare programs for the users based on its individual data and statics, and data modelling schemes generated based in the respiratory cloud service unit 30 and by using its application User Interface (UI). In addition, the respiratory cloud service unit 30 preferably provides Application Interface(s) (API) to transfer and receive related data to healthcare, wellbeing, and/or sport exercises application.

The respiratory cloud service unit 30 makes it possible for healthcare systems and professionals as well as trainers and individuals to collect, analysis and define tailored treatment and training programs that could be offered in real-time, anywhere, any time.

It also makes it possible to offer users means to follow their life-time data and programs to care of their respiratory heath and overall wellbeing and performance.

Also, respiratory cloud service unit 30 can be used to integrate the detected data. In accordance with an embodiment, respiratory $CO_2$ emission, oximetry probe $SpO_2$, and fluctuation of electrocardiogram (ECG), heart rate and its variation data are combined and analysed. Further, the respiratory cloud service unit 30 can be used to integrate and analyse the detected data.

The collected and analyzed data can contain different parameters, such as
respiratory time,
variation of airflow,
Lung Total Capacity (LTC), and
a respiration rate.

In accordance with an embodiment, this data is stored and analyzed, for example, in the device 1 and/or the respiratory cloud service unit 30.

The airflow temperature and its fluctuation can also be used to adjust the most suitable individual airflow temperature of the device 1.

The method can comprise the following step:

using history data of the calculated amount of energy gained during the inhaling and/or the calculated amount of energy used during the exhaling to define the user airflow resistance profile.

In addition or alternatively, the method comprises the following step using history data of the maximal inspiratory pressure (MIP), the maximal expiratory pressure (MEP), the maximal inspiratory flow (MIF), and the maximal expiratory flow (MEF) to define the user airflow resistance profile.

In addition or alternatively, the method comprises the following step using history data of the tidal volume (TV), inspiratory reserve volume (IRV), expiratory reserve volume (ERV), residual volume (RV), and/or Lung Total Capacity to define the user airflow resistance profile.

In accordance with an embodiment, the method comprises recommending a preferred resistance step for an individual (i.e., the user), based on, for example, the history data and a reference data defined based on the airflow resistance in the device 1.

The system can comprise:

means for defining the user profile using the history data, such as means for defining the user airflow resistance profile using the history data, and means for showing a preferred value for a user, for example, means for showing a preferred flow resistance step for the user, such as the display 27, wherein the recommendation is based on the history data and reference parametric data defined based on, for example, the airflow resistance in the device 1.

By using the recommended data, the user can select the most appropriate adjustments, such as temperature and/or airflow step adjustment(s).

The most appropriate airflow step adjustment can be implemented with adjusting means 29, for example, mechanically, for example, by using a peripheral adjuster, or automatically, for example, by selecting the option in the user interface of the software application via which the step is adjusted automatically.

The recommended airflow resistance step data can be stored and displayed using a display 27 of the device 1.

In accordance with an embodiment, the moisture rate of the inhale airflow is measured and utilized to adjust the resistance/moisture rate and temperature. Thus, it is possible to open and moisturize airways efficiently, which may lead to strengthened respiratory muscles. The device 1 trains inhalation and exhalation muscles with the adjustable breathing resistance. The device 1 also produces warm molecular water vapor into the airways.

Due to the above-mentioned measurements and analysis, a user may be offered with future treatment and exercise plans and recommendations. For this purpose, network infrastructure and applications are preferably used to provide said plans and recommendations to users.

In accordance with an embodiment, the integrated pressure and airflow monitoring and control unit (PAM) monitors the inhaled and exhaled airflows, controls and adjusts the recommended personalized airflow and further offers the display of data and biofeedback.

In accordance with an embodiment, once measured data is analyzed, it is displayed locally in a display 27 of the device 1 for rapid biofeedback, and/or displayed by using the wireless device application, and/or transmitted to the backbone network using transmitting means 28, for example, over a radio system air interface.

The above disclosed respiratory data collection, monitoring and analyzing method and system may bring unprecedented possibilities to collect, analyze and follow up the personalized respiratory data and promote the wellbeing and performance of users.

The method and system according to the aspects of the disclosed embodiments may make the current lung function tests much more flexible, efficient and accurate as well as traceable. It may help in-time diagnosing of breathing problems such as asthma and chronic obstructive pulmonary disease (COPD). In addition, it may bring versatile respiratory services and support to the wide range of users, helping them to improve their wellbeing. It may help to easily exercise the breathing, following up breathing conditions and improve it systematically based on the history, reference and training data.

The device 1 according to the aspects of the disclosed embodiments can be used in a variety of situations to help the subject's respiratory organs in their function. The device 1 is suitable for the care of, for example, asthma, allergies of the respiratory tract, chronic obstructive lung disease, as well as other pulmonary diseases, infections of the upper respiratory tract (cold), etc. By means of the device 1 according to the aspects of the disclosed embodiments, it is also possible for athletes to improve their performance, for example by strengthening their respiratory muscles and improving the function of their lungs, as well as by removing harmful mucus and opening the airways.

In some cases, the device 1 according to the aspects of the disclosed embodiments can also be applied for the care of animals. This may require some modifications in the structure of the device, while the principle of operation remains the same.

The use of the device 1 according to the aspects of the disclosed embodiments are not limited solely to the care of diseases, but the device 1 can also be used for improving the function of the respiratory organs of e.g. singers, voice users, etc. Because the device is suitable for use by persons of all ages as a form of care of e.g. cough and/or cold and, among other things, it may simultaneously strengthen the breathing mechanism, the device is suitable for use during a person's whole life span.

Although the aspects of the disclosed embodiments were described above by using the application of a warm liquid as an example in the care session, it is also possible to use a cold liquid in connection with the device 1. In some treatments or corresponding situations, it may be advantageous to use a cold liquid, even a liquid whose temperature is below 0 degrees. In such a situation, cold steam may rise from the liquid space, being conveyed to the subject's lungs during the inhalation step.

Furthermore, it should be noted that air was used as an example of the gas flow in the description of the present disclosure above, but it is obvious that in addition to air, the gas flow to be conveyed into and from the device may also comprise other substances than air, such as components evaporated from drugs.

The present disclosure is not limited to the above-presented embodiments, but it can be modified within the scope of the appended claims.

The invention claimed is:

1. A device for optimizing hyperthermia in airways comprising:
a first flow channel for inhalation;
a body part comprising an inner volume, wherein a first space of the inner volume is configured to be filled with liquid,
a second space of the inner volume being configured to receive steam forming in the first space of the inner volume, whereby the first flow channel is configured in a flow connection with the second space of the inner volume;
means for conveying a gas flow from the second space of the inner volume via the first flow channel to the outside of the device during inhalation;
a second flow channel arranged in a flow connection with the first space of the inner volume adapted to provide exhaled air into the liquid; and
means for conveying the exhaled gas flow from the outside of the device via the second flow channel to the first space of the inner volume to increase pressure in the inner volume, wherein the device further comprises:
means for measuring a flow and a temperature of an airflow,
means for calculating a first index based on measuring the flow and the temperature, wherein at least one of:
an amount of energy gained during an inhaling, and
an amount of energy used during an exhaling, is used for the calculation of the first index; and
means for adjusting the flow of the airflow is one or more of manually or automatically based on the first index, for optimizing the hyperthermia in airways.

2. The device according to claim 1, wherein
the means for conveying the gas flow from the second space via the first flow channel to the outside of the device comprises a first valve, wherein the first valve is closed by underpressure, and/or
the means for conveying the gas flow from the outside of the device via the second flow channel to the first space comprises a second valve, wherein the second valve is closed by underpressure.

3. The device according to claim 2, wherein the device further comprises:
means for transmitting at least some of the measured data.

4. The device according to claim 1, wherein the means for measuring the flow and the temperature of the airflow comprise:
a first sensor for measuring the flow of the airflow, and
a second sensor for measuring the temperature of the airflow.

5. The device according to claim 1, wherein the device also comprises a third flow channel, to which the first flow channel and the second flow channel are connected in such a way that conveying the gas flow from the outside of the device to the second flow channel and conveying the gas flow from the first flow channel to the outside of the device are arranged via the third flow channel.

6. The device according to claim 1, wherein the device also comprises one or more of:
heating means for heating the liquid in the first space, or
pressurizing means for increasing the pressure in the first space.

7. The device according to claim 1, wherein at least one of:
tidal volume (TV),
inspiratory reserve volume (IRV),
expiratory reserve volume (ERV),
residual volume (RV),
lung total capacity (LTC), and
Heart rate variation,
is used for the calculation of the first index.

8. The device according to claim 1, wherein the device comprises means for determining:
a maximal inspiratory pressure (MIP),
a maximal expiratory pressure (MEP),
a maximal inspiratory flow (MIF), and
a maximal expiratory flow (MEF) of an individual.

9. A method comprising:
conveying exhaled air via a second flow channel of a device to a first space of a body part of the device filled with a liquid,
forming steam in the first space due to the exhaled air;
receiving in a second space of the body part of the device steam formed in the first space;
conveying a gas flow from the second space via a first flow channel to the outside of the device during inhalation;
wherein the method further comprises:
measuring flow and temperature of at least one of an inhaled airflow and an exhaled airflow,
calculating an index based on measuring the flow and the temperature, wherein at least one of an amount of energy gained during an inhaling and an amount of energy used during an exhaling is used for the calculation of the index; and
adjusting flow resistance of at least one of the first flow channel and the second flow channel based on the index.

10. The method according to claim 9, wherein the method further comprises:
analyzing the measured flow and temperature of at least one of the inhaled airflow and the exhaled airflow, wherein the analyzing comprises calculating values of:
the amount of energy gained during an inhaling,
the amount of energy transferred during an exhaling,
a maximal inspiratory pressure (MIP),
a maximal expiratory pressure (MEP),
a maximal inspiratory flow (MIF), and/or
a maximal expiratory flow (MEF),
and the method further comprises:
recommending a preferred resistance step for an individual based on the analysis using at least one of the calculated values.

11. The method according to claim 10, wherein the method further comprises:
transmitting at least some of measured flow and temperature data and/or analyzed measured flow and temperature data to a respiratory cloud service unit.

12. A system comprising:
a device comprising:
a first flow channel for inhalation;
a body part comprising an inner volume, wherein a first space of the inner volume is configured to be filled with a liquid,
a second space of the inner volume being configured to receive steam forming in the first space of the inner volume, whereby the first flow channel is arranged in a flow connection with the second space of the inner volume;

means for conveying a gas flow from the second space of the inner volume via the first flow channel to the outside of the device during inhalation;

a second flow channel arranged in a flow connection with the first space of the inner volume configured to provide exhaled air into the liquid;

means for conveying the exhaled gas flow from the outside of the device via the second flow channel to the first space of the inner volume to increase pressure in the inner volume, measurement means for measuring a flow and a temperature of an inhaled airflow;

means for calculating an index based on measuring the flow and the temperature, wherein at least one of an amount of energy gained during an inhaling and an amount of energy used during an exhaling is used for the calculation of first index; and wherein the system further comprises:
an integrated pressure and airflow monitoring and control unit comprising:
a wireless component,
a processor, and
at least one memory component.

13. The system according to claim 12, wherein the system further comprises a display configured to show recommendations to a user.

14. A device for optimizing hyperthermia in airways comprising:
a first flow channel for inhalation;
a body part comprising an inner volume, wherein a first space of the inner volume is configured to be filled with liquid,
a second space of the inner volume being configured to receive steam forming in the first space of the inner volume, whereby the first flow channel is configured in a flow connection with the second space of the inner volume;
means for conveying a gas flow from the second space of the inner volume via the first flow channel to the outside of the device during inhalation;
a second flow channel arranged in a flow connection with the first space of the inner volume adapted to provide exhaled air into the liquid; and
means for conveying the exhaled gas flow from the outside of the device via the second flow channel to the first space of the inner volume to increase pressure in the inner volume, wherein the device further comprises:
means for measuring a flow and a temperature of an airflow,
means for calculating a first index based on measuring the flow and the temperature, wherein at least one of:
a tidal volume (TV),
an inspiratory reserve volume (IRV),
an expiratory reserve volume (ERV),
a residual volume (RV),
a lung total capacity (LTC), and
Heart rate variation,
is used for the calculation of the first index; and
means for adjusting the flow of the airflow is one or more of manually or automatically based on the first index, for optimizing the hyperthermia in airways.

* * * * *